US009242056B2

(12) United States Patent
Andersen et al.

(10) Patent No.: US 9,242,056 B2
(45) Date of Patent: Jan. 26, 2016

(54) ACOUSTIC INHALER FLOW MEASUREMENT

(75) Inventors: Bjørn Knud Andersen, Struer (DK); Svend-Erik Poulsen, Struer (DK)

(73) Assignee: Bang & Olufsen Medicom A/S, Struer (DK)

(*) Notice: Subject to any disclaimer, the term of this patent is extended or adjusted under 35 U.S.C. 154(b) by 1622 days.

(21) Appl. No.: 12/224,222

(22) PCT Filed: Feb. 28, 2007

(86) PCT No.: PCT/DK2007/000101
§ 371 (c)(1),
(2), (4) Date: Oct. 21, 2008

(87) PCT Pub. No.: WO2007/101438
PCT Pub. Date: Sep. 13, 2007

(65) Prior Publication Data
US 2009/0308387 A1 Dec. 17, 2009

(30) Foreign Application Priority Data

Mar. 7, 2006 (DK) ................................ 2006 00331
Apr. 20, 2006 (DK) .............................. 2006 000548

(51) Int. Cl.
*A61M 15/00* (2006.01)
*A61M 16/00* (2006.01)
*G01F 1/66* (2006.01)

(52) U.S. Cl.
CPC .......... *A61M 15/0065* (2013.01); *A61M 15/00* (2013.01); *A61M 2016/0039* (2013.01); *A61M 2202/064* (2013.01); *A61M 2205/3375* (2013.01); *G01F 1/666* (2013.01)

(58) Field of Classification Search
CPC . A61M 11/00; A61M 11/001; A61M 11/007; A61M 15/00; A61M 15/0001; A61M 15/0065; A61M 15/008; A61M 16/0003; A61M 2016/0027; A61M 2016/003; A61M 2016/0033; A61M 2016/0015
USPC ............. 128/203.15, 203.12, 200.14, 200.24, 128/202.22, 204.21, 204.22, 200.23
See application file for complete search history.

(56) References Cited

U.S. PATENT DOCUMENTS 5,505,195 A 4/1996 Wolf et al.
5,819,726 A * 10/1998 Rubsamen et al. ...... 128/200.14
(Continued)

FOREIGN PATENT DOCUMENTS

EP 1 480 555 12/2004
GB 2 262 452 6/1993
(Continued)

OTHER PUBLICATIONS

Rabbani K S et al: "A novel gas flow sensor based on sound generated by turbulence Yand spirometry application" May 19, 1997, Instrumentation and Measurement Technology Conference, 1997.IMTC/ 97. Proceedings. Sensing, Processing, Networking., IEE Ottawa, Ont., Canada May 19-21, 1997, New York, NY, USA, IEEE, US, pp. 1386-1388, XP010233794 ISBN: 0/7803-3747-6 the whole document.

*Primary Examiner* — Justine Yu
*Assistant Examiner* — Colin W Stuart
(74) *Attorney, Agent, or Firm* — Harness, Dickey & Pierce, P.L.C.

(57) ABSTRACT

A dry powder or aerosol inhaler having attached thereto, in a detachable manner, a sound/vibration sensor adapted to sense sound/vibration in the interval of 100-3000 Hz and there from derive a parameter of a flow in a flow path of the inhaler. The sensor does not interfere with the flow path of the inhaler.

16 Claims, 4 Drawing Sheets

(56) References Cited

U.S. PATENT DOCUMENTS

| | | |
|---|---|---|
| 2001/0028371 A1* | 10/2001 | Su et al. .......................... 347/19 |
| 2004/0069301 A1 | 4/2004 | Bacon |
| 2005/0183725 A1* | 8/2005 | Gumaste et al. ......... 128/203.15 |
| 2005/0268908 A1* | 12/2005 | Bonney et al. ........... 128/203.15 |
| 2007/0017506 A1* | 1/2007 | Bell et al. ................ 128/200.23 |
| 2007/0056585 A1* | 3/2007 | Davies et al. ............ 128/203.15 |

FOREIGN PATENT DOCUMENTS

| | | |
|---|---|---|
| GB | 2 398 065 | 8/2004 |
| WO | WO 2005/042076 | 5/2005 |

* cited by examiner

ACOUSTIC INHALER FLOW MEASUREMENT

FIELD OF THE INVENTION

The present invention relates to the field of analyzing, monitoring, logging and transmitting information on inhaler-based medication history. Such information may be used for clinical trials, where the use pattern versus prescription of an inhaler based drug is an important parameter, or the information feedback may be displayed directly to the user to guide the user to better inhalation and compliance.

More specifically this invention relates to a device, which may be attached to an existing inhaler without any need of intervention within the function of the inhaler. The inhalation flow is measured acoustically outside the inhaler by means of a microphone or similar acoustic/vibration sensor. Additionally, means for measuring dose loading externally from the device will be disclosed.

BACKGROUND OF THE INVENTION

Inhalers have become wide spread for treating i. e. respiratory disorders, diabetes, osteoporosis and pain. The inhaler devices are clinically validated together with the specific drug for a specific therapy. When new issues come up that need to be clinically substantiated combined with a need of better clinical cost/benefit ratio by obtaining more reliable use pattern data from fewer test persons, or there is a need for new features like compliance feedback to the user, there is a demand for implementing electronic event data logging with inhalers. To avoid redesigning the inhalers and the associated costly clinical trials, there is a need for an add-on device, which does not imply any intervention into the inhaler, thus still logging or providing relevant reliable data regarding dose loading and inhalation flow.

U.S. Pat. No. 5,505,195 describes an electronic device to be attached to a standard dry powder inhaler, but the description reveals that the flow sensors disclosed interfere with the mechanical design of the inhaler and will therefore not conform to the demands above. GB-2262452 discloses several techniques for flow measurements within inhalers, but they all measure the flow inside the inhaler flow path and will therefore not conform to the above requirements. Other inhalers may be seen in US2004/0069301 and GB2398065. There is, therefore, a need of an invention to solve and fulfil the demand for a true non-intervening add on monitoring device for existing inhalers.

SUMMARY

It is an object of the present invention to provide a simple add-on electronic monitoring device to be attached to an existing conventional inhaler design without the need of changing the design and risk of changing the aerodynamic behaviour of the inhaler flow path. The monitoring device may contain acoustic sensors, detectors, control circuit, data transmission circuit, battery, display or diodes and optional circuits for indirectly detecting dose loading in the inhaler.

In a first aspect, the invention relates to a dry powder or aerosol inhaler comprising an external surface and:
  means for dispensing a dry powder or an aerosol at a dispensing position,
  means for defining a flow path between the dispensing position and an outlet,
  sensing means detachably attached to the external surface, the sensing means being adapted to sense vibrations or sound with a frequency in the interval of 100-3000 Hz and estimate, on the basis of the vibrations/sound sensed, a parameter of a flow in the flow path.

In the present context, an aerosol normally is a medication, such as a dry powder, suspended, in a canister, in a medium adapted for expelling the powder. A dispenser of this type often is termed a pMDI (pressurixed metered dose inhaler).

Both the dry powder and the aerosol is inhaled by the person by the person drawing air through the inhaler and in the flow path, past the dispensing position, out the outlet and into the lungs of the person. In this situation, the gas flow and other gas parameters may be those of the mixture of air and powder/aerosol, which is output of the output and inhaled by the person.

Normally, the dispensing position and the flow path form parts of an overall flow path in the inhaler from one or more air Intakes, past the dispensing position and to the gas outlet which normally is shaped so that it is easily engaged or sealed against by the lips of a person.

The flow path is defined by surfaces, normally internal surfaces, of the dispenser, the external surface to or at which the sensing means is attached does not form part of the surfaces defining the flow path.

The sensing means should be detachably attached to the external surface in a manner so that, if removed, no impact is made on the aerodynamic behavior or properties of the flow path. In that manner, the medical compliance of the inhaler is not affected by the presence (or absence) of the sensing means.

The attachment may be an attachment via which the acoustic vibrations or sound travels from the external surface to the sensor (an acoustic attachment).

It is well known from acoustics that sound travels well in most solid materials. When a user inhales the medication, the flow path within the Inhaler creates a characteristic flow noise sound depending on flow rate and turbulences. Some of this sound is transmitted through the solid structure of the inhaler. As losses in the solid material are small, it is in principle possible to detect the sound anywhere on the Inhaler surface. It has been found that the optimal frequency interval for such flow determination is 100-3000 Hz, such as in the 600-900 Hz interval.

A number of parameters may be interesting, depending on the medication to be inhaled and other situations such as the age or training of the person.

One parameter is the volume of gas/air inhaled. This parameter may be used for ensuring that a sufficient amount of medication was inhaled.

Another parameter is the flow velocity of the gas. It has been found that depending on where the medication is to be deposited (throat, lungs), the velocity of the inhaled gas/particles must be different. Thus, the flow velocity may be of interest in the determination whether the inhalation was correct.

Other interesting parameters may be the time during which the flow was within a certain flow velocity interval or above a certain lower limit, again to ensure that the inhalation was correct or sufficient.

In fact, the present dispenser may also be used for estimate, on the basis of the vibrations/sound sensed, a maximum flow output from the gas outlet. Thus, a peak flow inspiratory sensor is obtained.

The present sensor may also be used for detecting other events or features of the dispenser or the dispensing. In one situation, the sensor is used for detecting inhaler dose loading mechanism sounds. Thus, also the correct loading or the time between loadings and dispensing may be determined or logged for later evaluation.

Even though any type of noise/sound/vibration sensor may be used, it is preferred that the present sensor is chosen from the group consisting of: a microphone, a strain gauge, a piezo element, an accelerometer, a bending sensor, capacitive sensor, a magnetic sensor, a displacement sensor, and an optical sensor.

In order to be able to cancel out ambient noise or handling noise, In one situation, the sensor further comprises another acoustic sensor for measurement of, and in communication with the surroundings. Thus, the signal from this other sensor may be used for eliminating ambient noise or handling noise from the signal from the actual sensor.

In another situation, the sensor comprises an ambient noise reducing acoustic sensor design, where the front of the sensor is brought into direct contact with the exterior surface of the inhaler, and where the rear side of the sensor Is in direct acoustic communication with the surroundings via a port in a casing enclosing the sensor, thereby cancelling ambient noise directly in the sensor.

A control circuit may be used for obtaining the parameters from the sensor and for calculating, estimating or determining information relating to the use of the inhaler. This information may be information relating to:
- after an inhalation, whether the inhalation was correct, such as if the duration, power consistency and frequency spectrum fulfils certain requirements,
- the time of inhalation—such as for compliance determination, or
- inhalation flow rates.

Naturally, the information derived may be used in a number of manners. In one situation, the inhaler further has means for informing a user of one or more estimated parameters. These means may be integral with the sensing means so as to be removable from one inhaler and attachable to another, such as when one inhaler, or a powder/aerosol container thereof, is used up.

These means may further comprise data communication means for communication with e.g. a computer or a device adapted to forward information from the inhaler/sensing means to a doctor or other person for analysis and evaluation. This information may both be information relating to a newly performed inhalation (such as for training purposes) or stored information relating to the use over a period of time, such as for statistical analysis or compliance determination.

In a preferred example embodiment, the inhaler has a dry powder container or an aerosol container and a first part defining at least part of the flow path. In that manner, the container may be replaced while maintaining the first part of the inhaler. If the first part defines all of the flow path, the aerodynamic properties thereof will not change when replacing an empty container.

In a first situation, the external surface is an outer surface of the container, whereby the sensor is removed before discarding an empty container. In another situation, the external surface is an outer surface of the first part, whereby the sensor need not be removed when replacing a container.

The optimum position of the sensor will depend on the construction of the inhaler and the materials of which it is made. The vibrations caused by flow in the flow channel will travel through all materials but with different efficiency depending on the actual material and the construction of the inhaler. Presently, it is preferred to position the sensor in contact with a surface part which is allowed to and adapted to vibrate with a frequency in the interval of 100-3000 Hz in that the vibration of this part during a flow will amplify the sound or vibration sensed by the sensor.

Desirably, the position of the sensing means is chosen to be one where the desired parameter (such as the flow rate) may be determined. Thus, the position may be one in which the sound or vibration is sufficiently high/large, where variations during manufacturing influence the measurements the least or below a desired limit, and/or where no or only insignificant impact on the flow path is made. Also, aesthetics and ergonomics may be taken into account when determining the position.

Another aspect of the invention relates to a method of operating the above inhaler, the method comprising sensing vibration(s) or sound with one or more frequencies within the interval of 100-3000 Hz and, estimating, on the basis of the sensed vibration/sound, a parameter of a flow in the flow path.

One such estimated parameter may be a volume of gas output from the gas outlet. The strength or amplitude of the sound/vibration, such as at one or more frequencies or frequency Intervals, is dependent on the flow (volume per time unit) of the gas/air flowing. Thus, the flow may be determined rather simply.

Another such parameter may be a maximum flow output from the gas outlet. Thus, the above-mentioned peak flow inspiratory sensor may be obtained.

A third such parameter may be a period of time during which a predetermined flow has existed. Thus, it may be determined for how long, during a dispensation, the flow was over a certain threshold or within a predetermined flow interval.

The method may also comprise informing a user of one or more estimated parameters. This may be In order to train the person, inform the person of a compliance read-out, when the last inhalation took place, when the next inhalation should take place, how the person's peak inhalation flow has evolved, or the like.

Finally, a last aspect of the invention relates to a sensing means for use in the first aspect of the invention. Naturally, this sensing means may be adapted to perform all the above relevant operations, may be positionable at any desired position on the inhaler and may be attachable in any manner.

BRIEF DESCRIPTION OF THE DRAWINGS

In the following, preferred embodiments of the present invention are illustrated by reference to the drawing, wherein.

DETAILED DESCRIPTION OF EXAMPLE EMBODIMENTS

Figure 1:
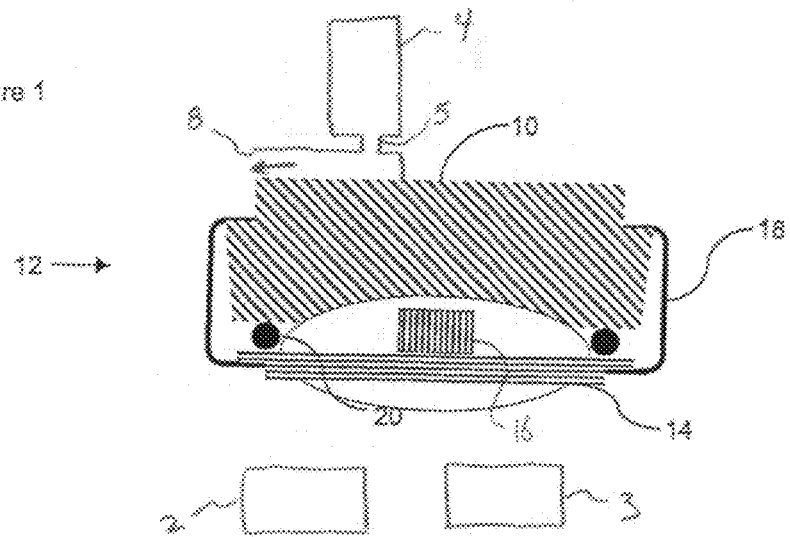
FIG. 1 illustrates a cross section of a first embodiment of an inhaler with a sensor.

FIG. 1 illustrates a cross section through a first embodiment of an inhaler 10, which may be any Inhaler, such as the Diskus® (GSK), Technohaler® (Innovata Biomed), D2L® (Ivax), Turbuhaler® (AstraZeneca), SkyeHaler DPI® (SkyePharma), Easi-Breathe DPI® (IVAX), Pulvinal® (Chiesi), EasyHaler® (Orion Farmos), Clickhaler® (Innovata Biomed), Taifun® (Focus Inhale), or the Ultrahaler®

(Aventis). At the bottom (or at any other suitable position), a sensor assembly 12 is provided which comprises an element 14 holding a microphone 16 and which is fastened via a fastening clip 18 to the bottom of the inhaler 10. Between the element 14 and the bottom, a resilient element 20 is provided for sealing airborne noise from the surroundings away from the microphone 16. The inhaler 10 may have a dispenser/container 4 for outputting medication at a dispensing position 5 from which the medication flows through a gas outlet 8. The sensor assembly 12 may further include a processor 2 and a display 3.

The space defined by the bottom, the element 20 and the element 14 forms a closed acoustic coupling volume between the microphone 16 and the inhaler, where the bottom acts as a "drum skin" and vibrates in a manner so that the microphone 16 may detect the vibration.

In another embodiment, a second microphone 30 is coupled to the surroundings in order to sense/detect the ambient noise in order to cancel out a potential ambient noise component in the signal from the first microphone and thereby achieve a detector system that is more robust to ambient noise sources present in the environment of the user during daily life situations.

Figure 2:
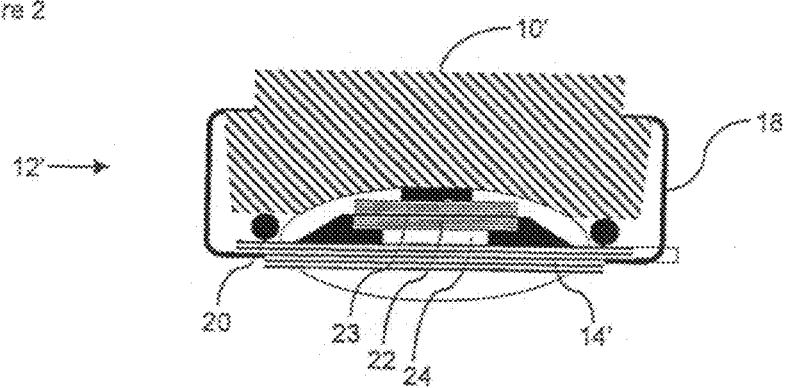
FIG. 2 illustrates a cross section of a second embodiment of an inhaler with a sensor.

FIG. 2 illustrates a cross section through a second embodiment of an inhaler 10' having a sensor 12' as seen in EP-A-1480555, "A transducer for bio-acoustic signals", which discloses a contact sensor 16' with a front side 23 and a rear side 22, the front side 23 being in solid communication with the source of sound (in this application the inhaler) and the rear side 22 being in communication with the surroundings through a port 24 in the sensor cover 14', said port 24 and cover 14' constituting an acoustic impedance that can optimize the ambient noise cancelling within the sensor 12'.

In general, the sensor 12/12' may be attached to the inhaler by the clip 18 and be removed there from such as to be attached to another dispenser 10/10'. It is also seen that the operation of the sensor 12/12' makes no impact on the flow path defined within the dispenser 10/10'.

Figure 3:
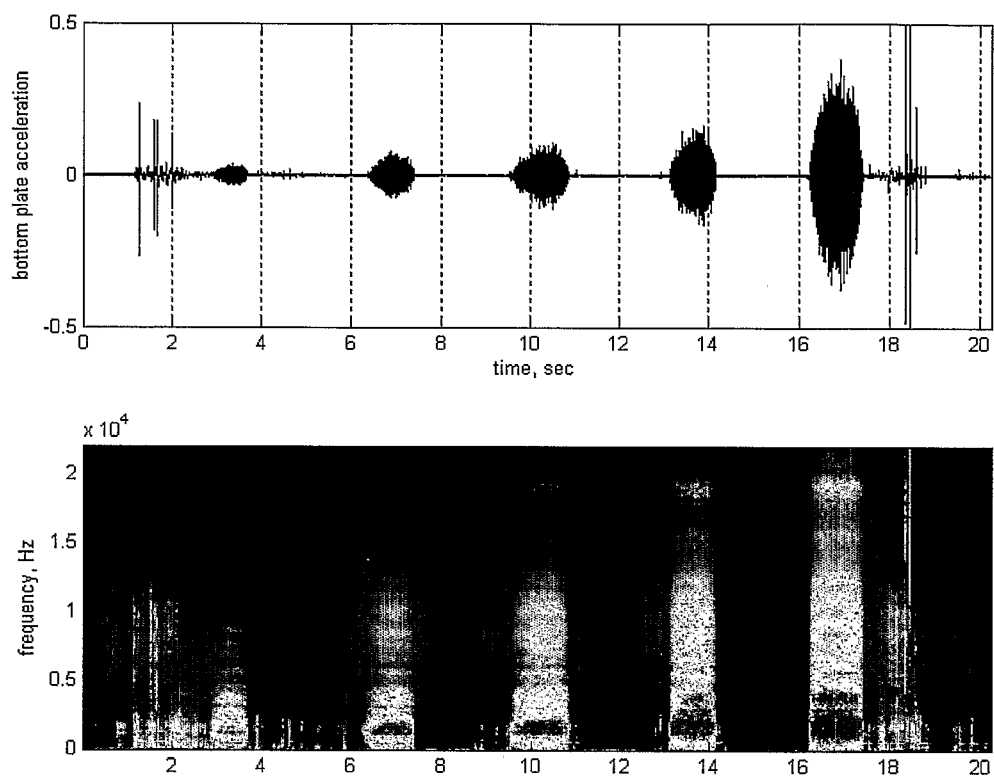
FIG. 3 illustrates the variation of a sound spectrum with flow rate.

The detected or sensed sound/vibration spectrum varies with the flow rate in the inhaler. In FIG. 3, results of experiments illustrate that the power/amplitude of sound at frequencies in the interval of 100-1000 Hz (Low range) essentially has a linear dependency with flow rate and the power of sound at frequencies in the Interval of 1000-5000 Hz (High range) has an essentially non-linear dependency with flow rate caused by increased turbulences and "whistle phenomena". Handling noise Is prominent in the low range of the frequency spectrum.

Thus, preferably, a method is devised for determining whether the noise/vibration/sound sensed relates to an inhalation or not. Numerous manners exist, one of which will be described in detail:

Preferably, the signal output from the sensor is filtered in order to obtain signal amplitude within particular frequency bands which are especially suitable for the individual dispenser. For e.g. the AstraZeneca TurbuHaler three frequency bands are used: X1: 600-900 Hz, X2: 2200-2280 Hz, and X3: 3500-5000 Hz.

FIG. 3 illustrates an experiment demonstrating the relationship between the inhalation flow in the mouthpiece of the dry powder inhaler and the associated structural acceleration picked up by the monitoring device. The inhaler is the AstraZeneca TurbuHaler and the acoustic sensing monitors the bottom plate vibration signal. A person now inhales at five times in succession (varying from 'very weak', 'weak', 'normal', 'strong' and 'very strong' inhalation where 'normal' approximately equals a flow rate of 30 l/min). As seen from the intensity/time plot the overall level of the vibrational signal follows the flow rate. Furthermore from the time/frequency plot it can be seen that the energy is not equally strong at all individual frequencies but follows structural resonances e.g. in the inhaler bottom plate mechanics.

In order to make sure that an inhalation takes place, the signals in all three bands is constantly logged, and when the signal energy in X3 exceeds that of X2 by a predetermined amount, and when the signal energy in X3 is above a predetermined threshold, an inhalation is assumed to take place, and the signal in X1 is logged and assumed to relate to a flow.

The actual flow relates to the energy in the X1 interval, whereby a determination of the actual flow, total volume inhaled, etc, is easy.

It may also be required that the flow (energy in X1) exceeds a predetermined threshold, before an inhalation is assumed to take place, and all three requirements may be required to take place simultaneously and continuously for a period of time, such as ½ second, before an inhalation is assumed to take place. In addition, if the requirements are fulfilled for a too long period of time, such as if the noise may be caused by e.g. an airplane, a vacuum cleaner or the like, the logging and measuring may be stopped and assumed invalid.

Naturally, any other manner of determining that an inhalation takes place may be used, such as manners based on more elaborate signal analysis adapted to e.g. detect an inhalation from a long-lasting (such as one or more seconds) relatively constant signal as compared to short-lasting handling noise. Also, other means may be required (such as rudimentary flow sensors already provided in the dispenser) for determining that an inhalation takes place and for trigging a flow measurement.

If necessary, further qualifying conditions may be set up to check for frequency balance between low and high frequency range.

Having thus obtained Information relating to the flow, different parameters may be obtained.

The energy in the X1 interval describes the flow over time. Thus, from the period of time in which the flow is within a predetermined flow Interval or exceeds a predetermined minimum flow, a quality of the inhalation may be derived, the amount of medication inhaled may be determined, or the volume of air/gas inhaled may be derived.

The volume of air/gas inhaled may also be derived on the basis of the full inhalation with no lower or upper limit for the gas flow.

The quality of an inhalation may be derived from the period of time during which the optimal flow is detected. Both a too low and a too high flow may be detrimental to this quality.

Also, the highest inhalation flow (peak inspiratory flow) may be determined from the sensed flow.

Naturally, any parameter sensed or determined may be read out to the user using a display, e.g. (not illustrated). Thus, the quality of the inhalation, the number of inhalations, compliance to a determined inhalation scheme, point in time of last or next inhalation, or similar information may be given to the person, such as quantified or qualified, in order for the user to easily see whether the inhalation or compliance is acceptable.

Also or alternatively, this information may be stored for later reading by e.g. clinical staff. This reading may be via wired or wireless communication (blue tooth, wireless, Ethernet, etc., etc.).

The sensor may also be used for additional detections. In one example, if the inhaler loader mechanism produces a characteristic acoustic signal/noise when activated, the above acoustic sensor systems may be used to detect a dose loading event that may be logged.

Thus, the time of loading may be compared to the time of inhalation, which may be interesting in some embodiments. Also, the user may be informed that a dose is loaded, and these points in time may be stored and read out for analysis of the compliance and behaviour of the person.

Naturally, the detection system may be combined with other types of sensors, such as an indirect dose loading detector, which may be a detector detecting a torque exerted between two parts of the inhaler body, which two parts are griped by the user when rotating two parts of the inhaler in relation to each other to load a next dose.

Figure 4:
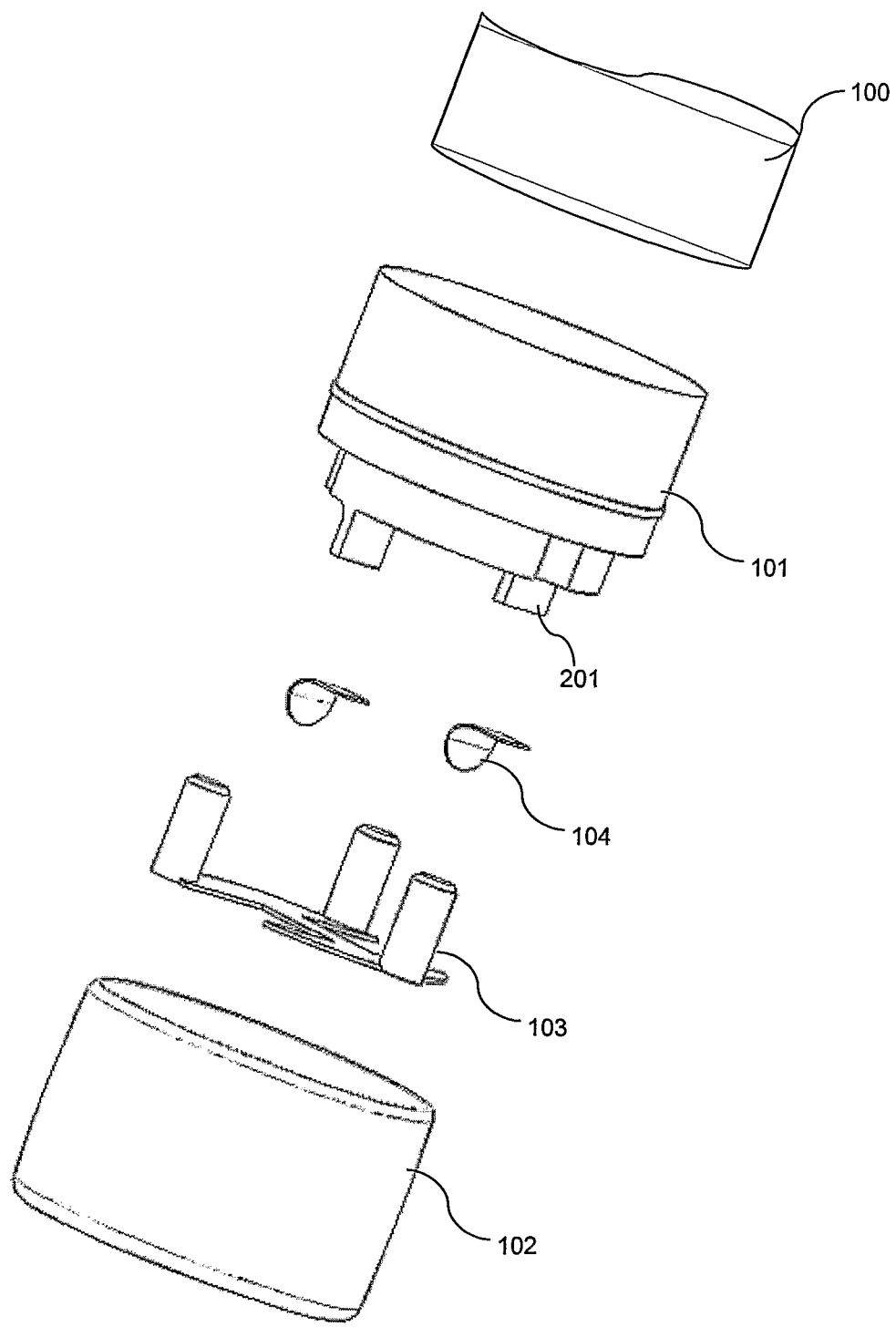
FIG. 4 illustrates an interesting manner of determining a torque between two elements.

FIG. 4 shows an exploded view of a torque measuring device assembly. Rotation of the part 100 in relation to the parts 101/102 will load a new dose in the dispenser 10.

This loading is performed by gripping the part 100 and the part 102 and rotating these elements. Between the parts 101 and 102, a torque sensing system is provided. The parts 101 and 102 are concentric bodies, rotatable in relation to each other, between which the torque is measured.

The torque is determined as one or more protrusions 201, 202 of each body, upon rotation, is forced toward each other. Between these protrusions, one or more force sensitive resistors (FSRs) 104 are positioned which provide a read-out relating to the torque.

To virtually avoid play between the two bodies, when assembled, without the risk of introducing friction between the bodies that could result in biasing the torque measurements, a resilient member 103 is fitted between the two bodies. In the present embodiment, two oppositely arranged FSRs are used for providing a bidirectional torque measurement; however, for a unidirectional torque measurement, only one FSR is required.

Figure 5:
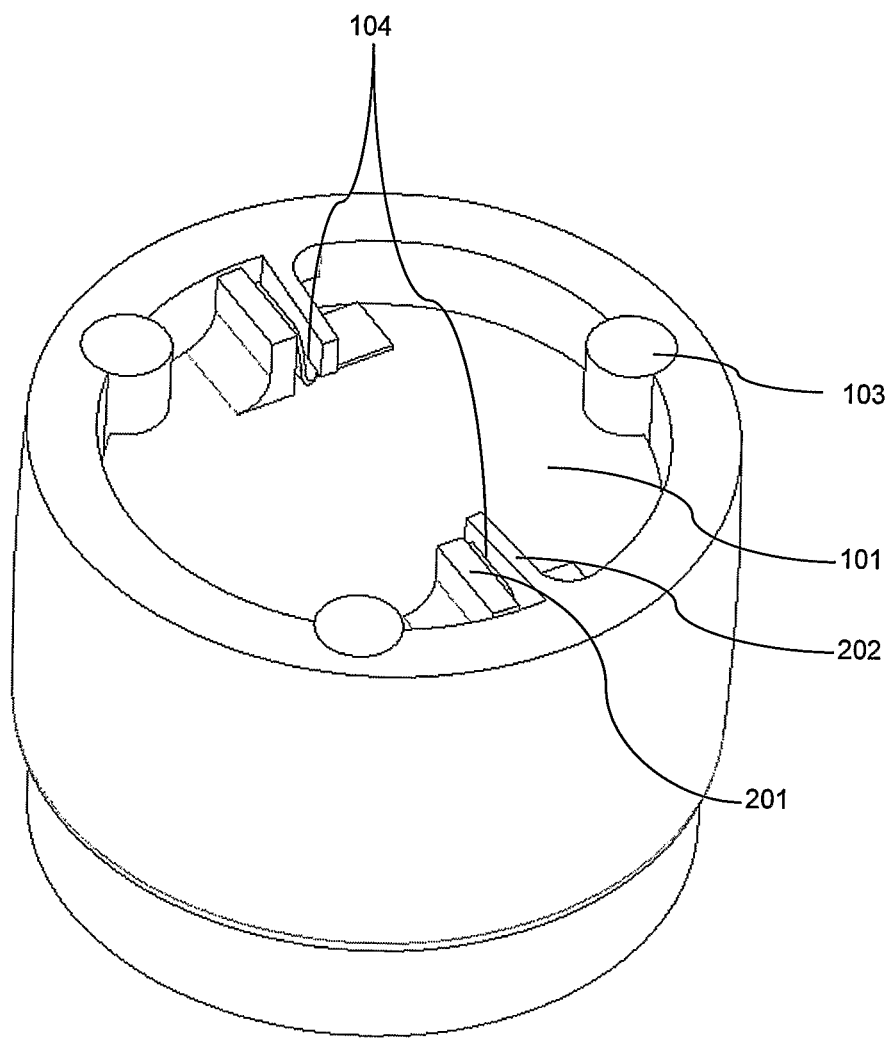
FIG. 5 illustrates a cross section through the embodiment of FIG. 4.

FIG. 5 shows a cross section of the torque measuring assembly of FIG. 4. FIG. 5 illustrates the protrusions 201 and 202 on the two bodies. These protrusions transfer the torque between the two bodies and the FSR mounted in between the protrusions will convert the force to a resistor value for further electronic registration of the torque.

Naturally, this type of torque measuring device may be used in many other types of systems, such as: break controls in vehicles, overload controls in cranes and other lifting equipment and safety controls in general.

In relation to the powder dispenser, as is the situation with the sound/vibration sensor, this sensor may be an add-on device which may be provided with no interference with the flow characteristics and thereby the clinical approval of the dispenser. Also, the device may be detachable and reusable with several dispensers. Naturally, if this sensor is not integral with the sound/vibration sensor, communication there between may be desired in order to gather the information from the two sensors as a single processor/storage/display.

The invention claimed is:

1. An inhaler, comprising:
    an external surface;
    a dispenser configured to dispense an aerosol or a dry powder at a dispensing position;
    a channel defining a flow path between the dispensing position and a gas outlet;
    a sensor detachably attached to the external surface, the sensor being adapted to sense vibrations or sound with a frequency in an interval of 100-3000 Hz;
    a processor adapted to estimate, on the basis of the vibrations/sound sensed in the interval of 100-3000 Hz, at least one parameter of a flow velocity of gas in the flow path; and
    a casing enclosing the sensor, wherein a front of the sensor is in direct contact with the external surface and a rear side of the sensor is in direct acoustic contact with surroundings of the inhaler via a port in the casing.

2. An inhaler according to claim 1, wherein the sensor is adapted to further estimate a volume of gas output from the gas outlet.

3. An inhaler according to claim 1, wherein the sensor is adapted to further estimate, as the at least one parameter, a maximum flow output from the gas outlet.

4. An inhaler according to claim 1, wherein the sensor is chosen from the group consisting of: a microphone, a strain gauge, a piezo element, an accelerometer, a bending sensor, capacitive sensor, a magnetic sensor, a displacement sensor, and an optical sensor.

5. An inhaler according to claim 1, further comprising a display device for informing a user of the at least one estimated parameter.

6. A method of operating an inhaler according to claim 1, the method comprising,
    sensing the vibrations or sound with at least one frequency within the interval of 100-3000 Hz; and
    estimating, on the basis of the sensed vibration/sound, the at least one parameter of the flow velocity of gas in the flow path.

7. A method according to claim 6, comprising estimating a volume of gas output from the gas outlet.

8. A method according to claim 6, comprising estimating, as the at least one parameter, a maximum flow output from the gas outlet.

9. A method according to claim 6, comprising estimating a period of time of the flow velocity of gas in the flow path.

10. A method according to claim 6, further comprising informing a user of the at least one estimated parameter via a display device.

11. A method according to claim 6, further comprising estimating a period of time during which the flow velocity was within a given flow velocity interval or above a given flow velocity limit.

12. A method according to claim 6, further comprising sensing ambient noise using a second acoustical sensor in communication with surroundings of the inhaler and eliminating ambient noise or handling noise on the basis of a signal from the second sensor.

13. An inhaler according to claim 1, wherein the sensor is adapted to further estimate a period of time of the flow velocity of gas in the flow path.

14. An inhaler according to claim 1, wherein the sensor is adapted to further estimate a period of time during which the flow velocity was within a given flow velocity interval or above a given flow velocity limit.

15. An inhaler according to claim 1, further comprising a second acoustical sensor in communication with surroundings of the inhaler and operative to sense ambient noise, the processor being adapted to receive a signal from the second acoustical sensor and eliminate ambient noise or handling noise from the signal from the second acoustical sensor.

16. A sensor for determining a flow velocity of gas in a flow path of a channel, the sensor comprising:
    a processor adapted to estimate, on a basis of a vibrations/sound sensed in an interval of 100-3000 Hz, at least one parameter of the flow velocity of gas in the flow path of the channel,
    wherein the sensor is configured to detachably attach to an external surface of an inhaler;
    the sensor being enclosed in a casing, wherein a front of the sensor is in direct contact with the external surface of the inhaler and a rear side of the sensor is in direct acoustic contact with surroundings of the inhaler via a port in the casing.

* * * * *